US011173038B2

United States Patent
Pak et al.

(10) Patent No.: US 11,173,038 B2
(45) Date of Patent: Nov. 16, 2021

(54) TOTAL ANKLE PROSTHESIS

(71) Applicant: Stryker European Operations Limited, Carrigtwohill (IE)

(72) Inventors: Chulho Pak, Mahwah, NJ (US); Subash K. Mannanal, Mahwah, NJ (US); Thomas Loring, Philadelphia, PA (US)

(73) Assignee: Stryker European Operations Limited

( * ) Notice: Subject to any disclaimer, the term of this patent is extended or adjusted under 35 U.S.C. 154(b) by 91 days.

(21) Appl. No.: 16/794,387

(22) Filed: Feb. 19, 2020

(65) Prior Publication Data

US 2020/0268520 A1    Aug. 27, 2020

Related U.S. Application Data

(60) Provisional application No. 62/809,141, filed on Feb. 22, 2019.

(51) Int. Cl.
| | | |
|---|---|---|
| *A61F 2/42* | (2006.01) | |
| *A61F 2/38* | (2006.01) | |
| *A61F 2/30* | (2006.01) | |

(52) U.S. Cl.
CPC .......... *A61F 2/4202* (2013.01); *A61F 2/385* (2013.01); *A61F 2/389* (2013.01);
(Continued)

(58) Field of Classification Search
CPC ............ A61F 2/4202; A61F 2002/4205; A61F 2002/4207
See application file for complete search history.

(56) References Cited

U.S. PATENT DOCUMENTS

| 3,872,519 A | 3/1975 | Giannestras et al. |
| 4,309,778 A | 1/1982 | Buechel et al. |
| (Continued) | | |

FOREIGN PATENT DOCUMENTS

| EP | 2165681 A1 | 3/2010 |
| GB | 1360485 A | 7/1974 |
| GB | 2108847 A | 5/1983 |

OTHER PUBLICATIONS

Extended European Search Report including Written Opinion for Application No. EP20157616.2, dated Jun. 4, 2020, pp. 1-5.
(Continued)

*Primary Examiner* — Javier G Blanco
(74) *Attorney, Agent, or Firm* — Lerner, David, Littenberg, Krumholz & Mentlik, LLP (57) ABSTRACT

A total ankle prosthesis that includes a talar component that has a bone contacting side for contacting a talus and an articular side opposite the bone contacting side. The articular side has first and second condyles separated by an intercondylar notch. The first condyle defines a spheroidal convex surface. The prosthesis also includes a tibial component that has a bone contacting side for contacting a tibia and an articular side. The articular side has first and second condyles separated by an intercondylar spine. The first condyle of the tibial component defines a concave surface. The concave surface has a condylar edge that defines a perimeter thereof and a plurality of articular portions positioned between anterior and posterior extents of the condylar edge. A first articular portion of the articular portions is spheroidal and a second articular portion is defined by a cylindrical helix.

18 Claims, 10 Drawing Sheets

(52) U.S. Cl.
CPC .............. *A61F 2002/30116* (2013.01); *A61F 2002/4205* (2013.01); *A61F 2002/4207* (2013.01)

(56) References Cited

U.S. PATENT DOCUMENTS

| | | | |
|---|---|---|---|
| 4,340,978 A | 7/1982 | Buechel et al. | |
| 4,470,158 A | 9/1984 | Pappas et al. | |
| 5,219,362 A | 6/1993 | Tuke et al. | |
| 5,413,604 A | 5/1995 | Hodge | |
| 6,013,103 A | 1/2000 | Kaufman et al. | |
| 6,056,779 A | 5/2000 | Noyer et al. | |
| 6,183,519 B1 | 2/2001 | Bonnin et al. | |
| 6,409,767 B1 | 6/2002 | Perice et al. | |
| 7,025,790 B2 | 4/2006 | Parks et al. | |
| 7,261,740 B2 | 8/2007 | Tuttle et al. | |
| 7,264,635 B2 | 9/2007 | Suguro et al. | |
| 7,309,362 B2 | 12/2007 | Yasuda et al. | |
| 7,485,147 B2 | 2/2009 | Pappas et al. | |
| 7,615,082 B2 * | 11/2009 | Naegerl | A61F 2/4202 623/21.18 |
| 7,625,409 B2 | 12/2009 | Saltzman et al. | |
| 7,678,152 B2 | 3/2010 | Suguro et al. | |
| 8,394,148 B2 | 3/2013 | Otto et al. | |
| 8,480,752 B2 | 7/2013 | Dun | |
| 8,636,807 B2 | 1/2014 | Komistek | |
| 8,696,755 B2 | 4/2014 | Mandell | |
| 8,764,838 B2 | 7/2014 | Parisi et al. | |
| 8,911,502 B2 | 12/2014 | Li et al. | |
| 9,107,769 B2 | 8/2015 | Samuelson et al. | |
| 9,132,018 B1 | 9/2015 | Hajianpour | |
| 9,662,217 B2 | 5/2017 | Heggendorn et al. | |
| 9,668,880 B2 | 6/2017 | Samuelson et al. | |
| 9,833,324 B2 | 12/2017 | Blaha | |
| 9,861,484 B2 | 1/2018 | Sanford et al. | |
| 9,925,054 B2 | 3/2018 | Siegler et al. | |
| 2006/0020345 A1 | 1/2006 | O'Connor et al. | |
| 2008/0009950 A1 | 1/2008 | Richardson | |
| 2010/0241237 A1 | 9/2010 | Pappas | |
| 2012/0185054 A1 | 7/2012 | Maloney et al. | |
| 2015/0190235 A1 | 7/2015 | McMinn | |
| 2016/0151162 A1 | 6/2016 | Wyss et al. | |
| 2016/0206437 A1 * | 7/2016 | Perler | A61F 2/4202 |
| 2016/0228255 A1 | 8/2016 | Samuelson et al. | |
| 2017/0007415 A1 | 1/2017 | Fiedler et al. | |
| 2017/0246004 A1 | 8/2017 | Goldberg et al. | |
| 2017/0266013 A1 | 9/2017 | Enomoto et al. | |

OTHER PUBLICATIONS

INFINITY Total Ankle System, Surgical Technique, WRIGHT Medical, pp. 1-76.
Integra Cadence Total Ankle System, Surgical Technique, pp. 1-60.
Integra Salto Talaris Total Ankle Prosthesis, Limit uncertainty with an anatomical design, Brochure pp. 1-6.
Integra Salto Talaris Total Ankle Prosthesis, Surgical Technique, pp. 1-36.
STAR Total Ankle Replacement, Operative Technique, Stryker Trauma & Extremities, pp. 1-32.

* cited by examiner

TOTAL ANKLE PROSTHESIS

CROSS-REFERENCE TO RELATED APPLICATIONS

This application claims the benefit of the filing date of U.S. Provisional Patent Application No. 62/809,141, filed on Feb. 22, 2019, the disclosure of which is hereby incorporated by reference.

BACKGROUND OF THE INVENTION

The human foot is capable of complex movements that are facilitated by the ankle. The ankle is comprised of multiple joints, including the tibiotalar or talocrural joint. The tibiotalar joint includes a distal end of a tibia and a proximal end of a talus which each have cartilaginous articular surfaces that articulate with each other to facilitate movement between the foot and leg. However, these articular surfaces can become damaged due to traumatic injury or worn due to disease, such as osteoarthritis.

Several prostheses have been developed that comprise tibial and talar components intended to replace the deficient joint. These prostheses each provide artificial articular surfaces that interact with each other to facilitate movement between the foot and leg. However, such articular surfaces often constrain the joint so as as to limit the degrees of freedom relative to that of the natural joint which results in an unnatural gait cycle. In addition, energy that cannot be relieved by relative movement between the joint components due to such constraints manifests itself as stress at the bone-component interface that can result in damage to the bone and component failure. Moreover, in order to facilitate articulation between the artificial joint components, the articular surfaces thereof are often shaped in such a way that the majority of the patient's weight undergoing dynamic movement is concentrated in very small areas which can lead to non-uniform and early wear of the artificial components which may require a revision procedure to rectify. Thus, further improvements are desirable.

BRIEF SUMMARY OF THE INVENTION

In one aspect of the present disclosure, a total ankle prosthesis includes a talar component that has a bone contacting side for contacting a talus and an articular side opposite the bone contacting side. The articular side has first and second condyles separated by an intercondylar notch. The first condyle defines a spheroidal convex surface. The prosthesis also includes a tibial component that has a bone contacting side for contacting a tibia and an articular side. The articular side has first and second condyles separated by an intercondylar spine. The first condyle of the tibial component defines a concave surface. The concave surface has a condylar edge that defines a perimeter thereof and a plurality of articular portions positioned between anterior and posterior extents of the condylar edge. A first articular portion of the articular portions is spheroidal and a second articular portion is defined by a cylindrical helix.

Additionally, the tibial component may include a tibial baseplate and a tibial insert may be connectable to the tibial baseplate. The tibial baseplate may include the bone contacting side of the tibial component and the tibial insert may include the articular side of the tibial component. The first condyle of the tibial component may be a medial condyle. Alternatively, the first condyle of the tibial component is a lateral condyle. The concave surface of the first condyle may have a third articular portion defined by the cylindrical helix that defines the first articular portion. The first articular portion may be positioned between the second and third articular portions. The concave surface may have fourth and fifth articular portions each being spheroidal. The fourth and fifth articular portions may be positioned so that they respectively intersect the anterior and posterior extents of the condylar edge. The second condyle of the tibial component may be arranged identically to that of the first condyle. The first, second, and third articular portions may each have a curvature that extends between lateral and medial extents of the condylar edge of the first condyle. The curvatures of the first, second, and third articular portions may each define a radius of curvature. The radii of curvatures of the first, second, and third articular portions may be equal. The second and third articular portions may slope downwardly in a posterior to anterior direction such that, when the tibial component is implanted, the second articular portion may be positioned more inferiorly than the third articular portion.

Continuing with this aspect, the curvature of the convex surface of the first condyle of the talar component may be such that, when the first condyle of the talar component articulates with the first condyle of the tibial component, a first interface between the first condyle of the talar component and the first articular portion forms area contact, and a second interface between the first condyle of the talar component and the second articular portion forms line contact that extends between lateral and medial extents of the condylar edge. The second condyle of the talar component may define a spheroidal convex surface, and the second condyle of the tibial component may define a concave surface that has a condylar edge defining a perimeter thereof and a first articular portion. The first articular portion of the second condyle may be spheroidal and has a curvature that extends from an anterior extent to a posterior extent of the condylar edge of the second condyle. The concave surface of the second condyle of the tibial component may include a second articular portion. The first articular portion of the second condyle of the tibial component may be spheroidal and the second articular portion of the second condyle of the tibial component may be defined by a cylindrical helix. Also, the spheroidal convex surface of each of the first and second condyles of the talar component may have an arc length in an anteroposterior direction longer than an arc length in a lateral-medial direction In another aspect of the present disclosure, a total ankle prosthesis include a talar component that has a bone contacting side for contacting a talus and an articular side opposite the bone contacting side. The articular side has lateral and medial condyles separated by an intercondylar notch. The lateral condyle defines a spheroidal convex surface. The prosthesis also includes a tibial component that has a bone contacting side for contacting a tibia and an articular side. The articular side has lateral and medial condyles separated by an intercondylar spine. The lateral condyle of the tibial component defines a concave surface that has a condylar edge that defines a perimeter thereof and a plurality of articular portions positioned between anterior and posterior extents of the condylar edge. A first articular portion of the articular portions is spheroidal such that it has a radius of curvature in both a coronal and sagittal plane, and a second articular portion of the articular portions is cylindrical such that it has a radius of curvature in a coronal plane but not in a sagittal plane.

Additionally, the radii of curvatures of the first and second articular portions in the coronal plane may be equal. The spheroidal convex surface of the lateral condyle of the talar component may be congruent with the first articular portion. The medial condyle of the talar component may define a spheroidal convex surface, and the medial condyle of the tibial component may define a concave surface having a condylar edge defining a perimeter thereof and a spheroidal articulation portion that extends between anterior and posterior extends of the condylar edge of the medial condyle. The spheroidal convex surface of the medial condyle may be congruent with the spheroidal articulation portion.

In an even further aspect of the present disclosure, a total ankle prosthesis includes a talar component that has a bone contacting side for contacting a talus and an articular side opposite the bone contacting side. The articular side has first and second condyles separated by an intercondylar notch. The first and second condyles each define a convex surface. The prosthesis also includes a tibial component that has a bone contacting side for contacting a tibia and an articular side. The articular side has first and second condyles separated by an intercondylar spine. The first condyle of the tibial component has a concave surface that has a condylar edge defining a perimeter thereof. The concave surface has a first articular portion positioned between anterior and posterior extents of the condylar edge. The first articular portion is defined by a cylindrical helix that that curves about an axis normal to the convex surface of the second condyle of the tibial component.

Additionally, the concave surface of the first condyle may define a second articular portion. The second articular portion may be spheroidal. The concave surface of the first condyle may include a third articular portion. The third articular portion may be spheroidal. The first articular portion may be positioned between the second and third articular portions. The second articular portion may have a greater anteroposterior length than the third articular portion. The second articular portion may intersect a posterior extent of the condylar edge, and the third articular portion may intersect an anterior extent of the condylar edge. The second condyle of the tibial component may be arranged identically to that of the first condyle of the tibial component. The second condyle of the tibial component has first, second, and third articular portions identical to the first, second, and third articular portions of the first condyle with the exception that the second articular portion may intersect an anterior extent of a condylar edge of the second condyle and the third articular portion may intersect the posterior extent of the condylar edge of the second condyle. The concave surface of the first condyle may include a third articular portion. The third articular portion may be defined by the cylindrical helix that defines the first articular portion. The second articular portion may be positioned between the first and third articular portions.

BRIEF DESCRIPTION OF THE DRAWINGS

The features, aspects, and advantages of the present invention will become better understood with regard to the following description, appended claims, and accompanying drawings in which:

DETAILED DESCRIPTION

When referring to specific directions in the following discussion of certain implantable devices, unless stated otherwise, it should be understood that such directions are described with regard to the implantable device's orientation and position during exemplary application to the human body. Thus, as used herein, the term "proximal" means close to the heart and the term "distal" means more distant from the heart. The term "inferior" means toward the feet and the term "superior" means toward the head. The term "anterior" means toward the front of the body or the face, and the term "posterior" means toward the back of the body. The term "medial" means toward the midline of the body, and the term "lateral" means away from the midline of the body. Also, as used herein, the terms "about," "generally" and "substantially" are intended to mean that slight deviations from absolute are included within the scope of the term so modified.

FIGS. 1A-6C depict a total ankle prosthesis 100 according to an embodiment of the present disclosure. The particular embodiment depicted is configured for a left leg. However, a right legged prosthesis would have the same features just mirrored from that of the depicted prosthesis 100. Prosthesis 100 includes a talar component or talar dome 110 and a tibial component 105. Tibial component 105 generally includes a tibial baseplate 120 and a tibial insert 130. Talar component 110 and tibial baseplate 120 are preferably made from a biocompatible metal, such as a stainless steel, titanium, cobalt-chromium, niobium, and alloys thereof, for example. Moreover, bone contacting surfaces thereof may be porous so as to encourage bone ingrowth. Tibial insert 130 is preferably made from a biocompatible polymer, such as Ultra High Molecular Weight Polyethylene (UHMWPE), for example.

Figure 1A:
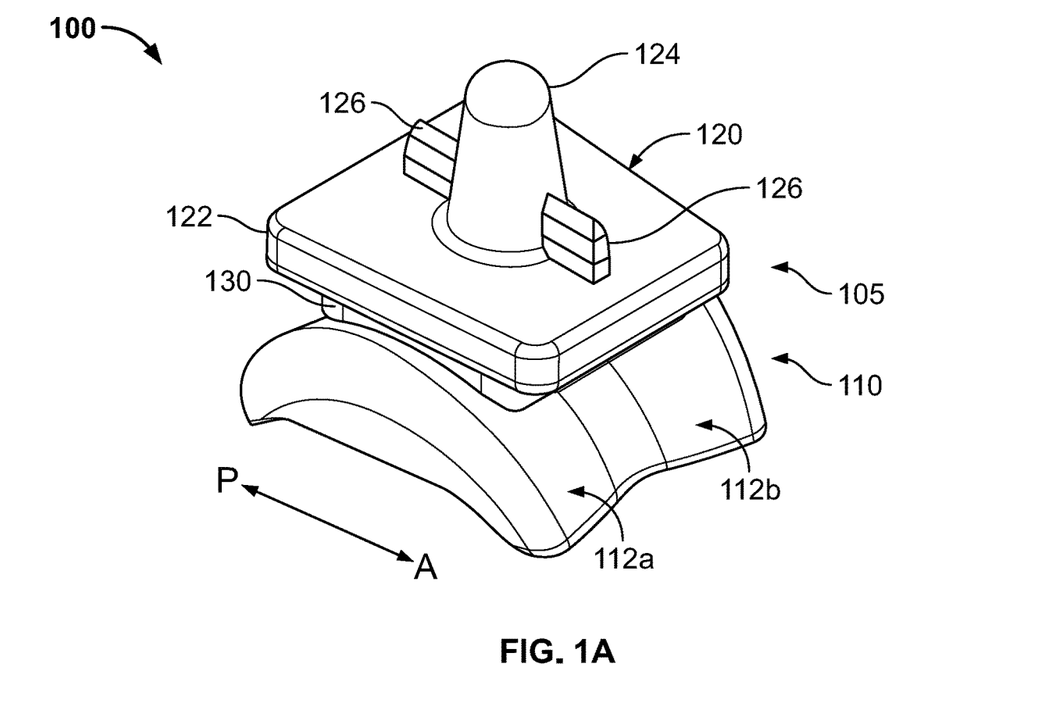
FIG. 1A is a rear perspective view of a total ankle prosthesis according to an embodiment of the present disclosure and including talar and tibial components.
Figure 1B:
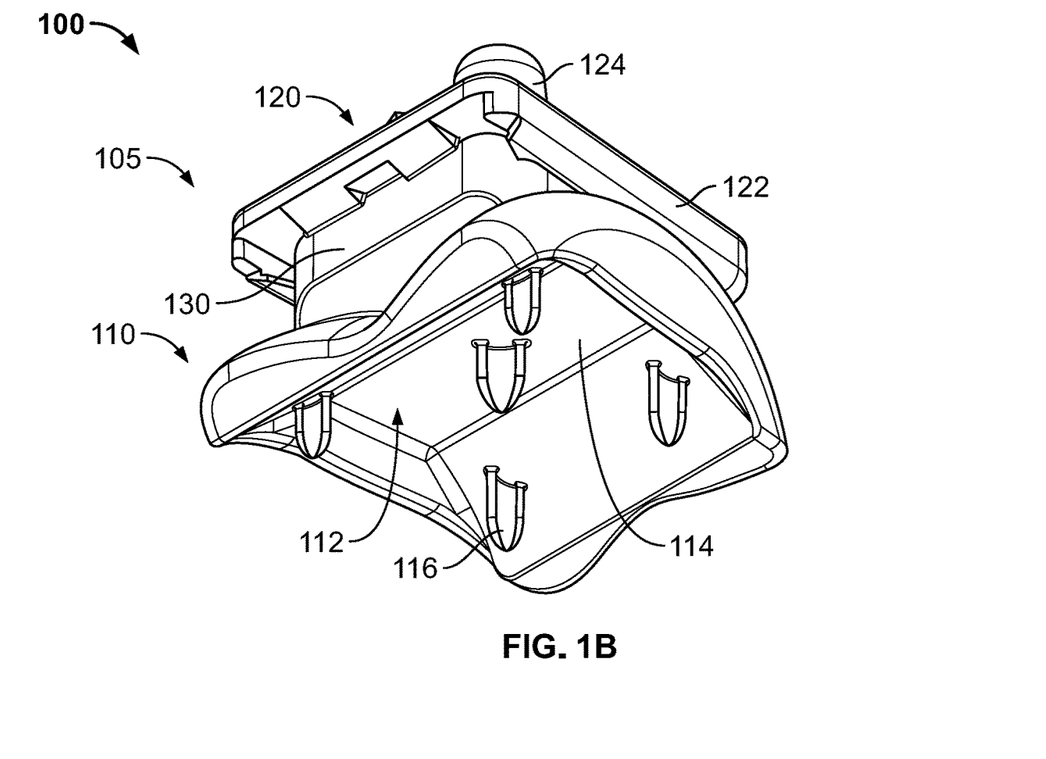
FIG. 1B is a front perspective view of the total ankle prosthesis of FIG. 1A.

Talar component 110 includes a bone contacting side and an articular side. The bone contacting side includes a recess 112 and a bone contacting surface 114 for contacting a resected talus, as best shown in FIG. 1B. In this regard, a talus is resected and talar component 100 is placed onto the resected talus like a cap such that the talus is received within recess 112. Bone engagement features or pegs 116 extend from bone contacting surface 114 for receipt in corresponding openings in the bone to help retain talar component 110 on the talus and prevent relative movement therebetween.

Figure 2A:
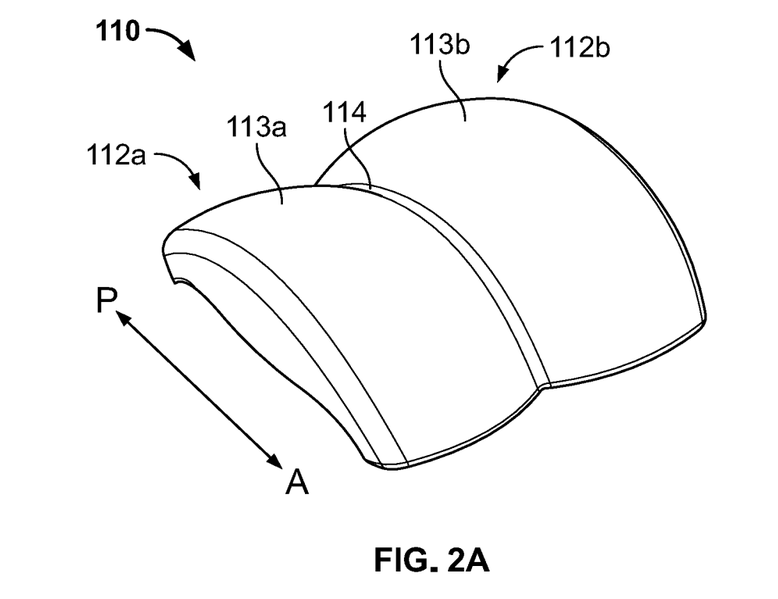
FIG. 2A is a front perspective view of the talar component of the total ankle prosthesis of FIG. 1A.
Figure 2B:
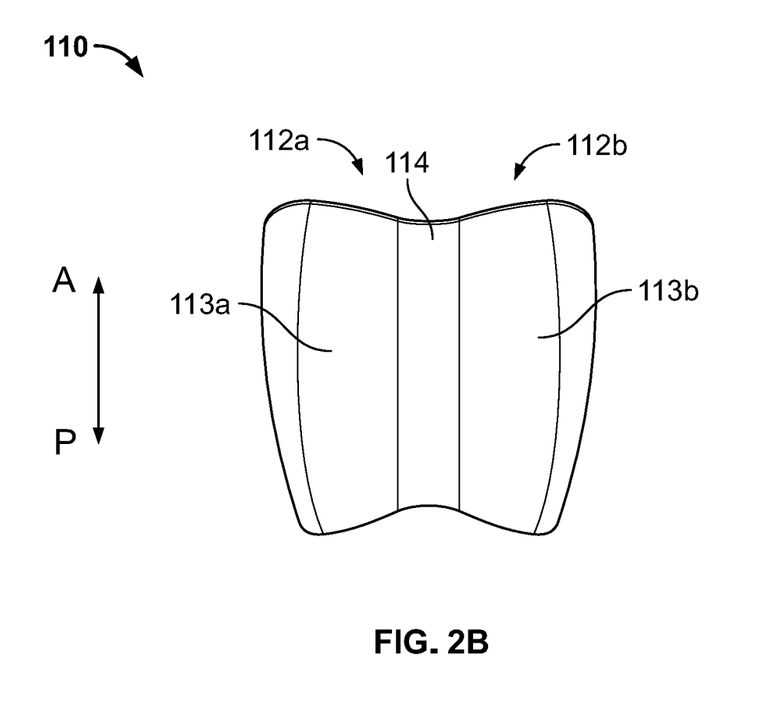
FIG. 2B is a top view of the talar component of FIG. 2A.
Figure 2C:
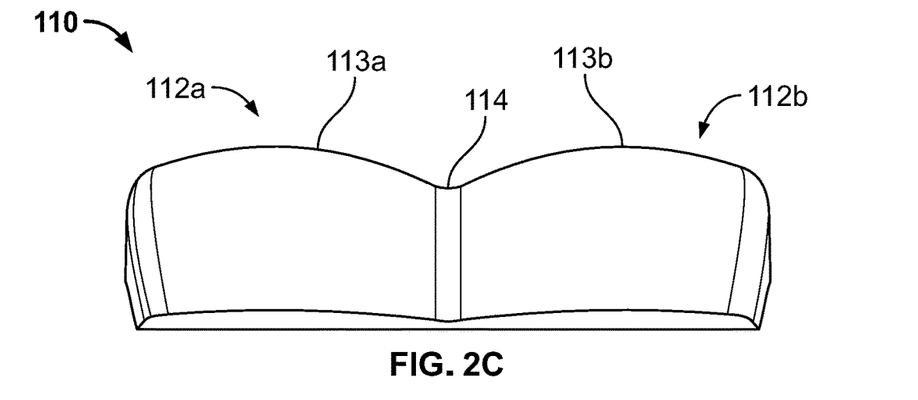
FIG. 2C is a rear elevational view of the talar component of FIG. 2A.
Figure 2D:
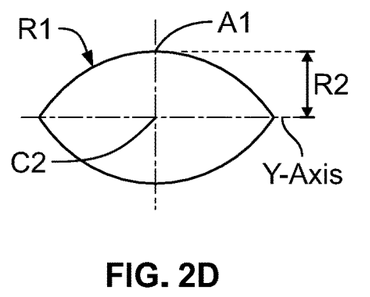
FIG. 2D is a rear elevational view of a spheroid that defines an articular surface of the talar component of FIG. 2A.
Figure 2E:
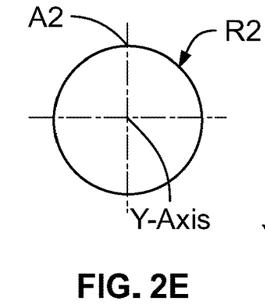
FIG. 2E is a side elevational view of the spheroid of FIG. 2D.
Figure 2F:
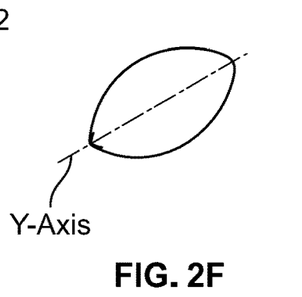
FIG. 2F is a perspective view of the spheroid of FIG. 2D.

The articular side of talar component 110 includes a first condyle or lateral condyle 112a and a second condyle or medial condyle 112b. The lateral and medial condyles 112a-b are convexly curved and are separated by an intercondylar notch 114 that extends along the length of talar component 110 in an anteroposterior ("A-P") direction. In the particular embodiment depicted, lateral and medial condyles 112a-b each include a spheroidal articular surface 113a-b. In this regard, articular surfaces 113a-b are each defined by a spheroid, particularly a prolate spheroid. Such prolate spheroid that defines the articular surfaces 113a-b is shown in FIGS. 2D-2F. As respectively shown in FIGS. 2D and 2E, the spheroid, just as articular surfaces 113a-b, are spherically curved in coronal and sagittal planes. However, a first radius of curvature R1 in the coronal plane is larger than a second radius of curvature R2 in the sagittal plane.

Figure 2G:
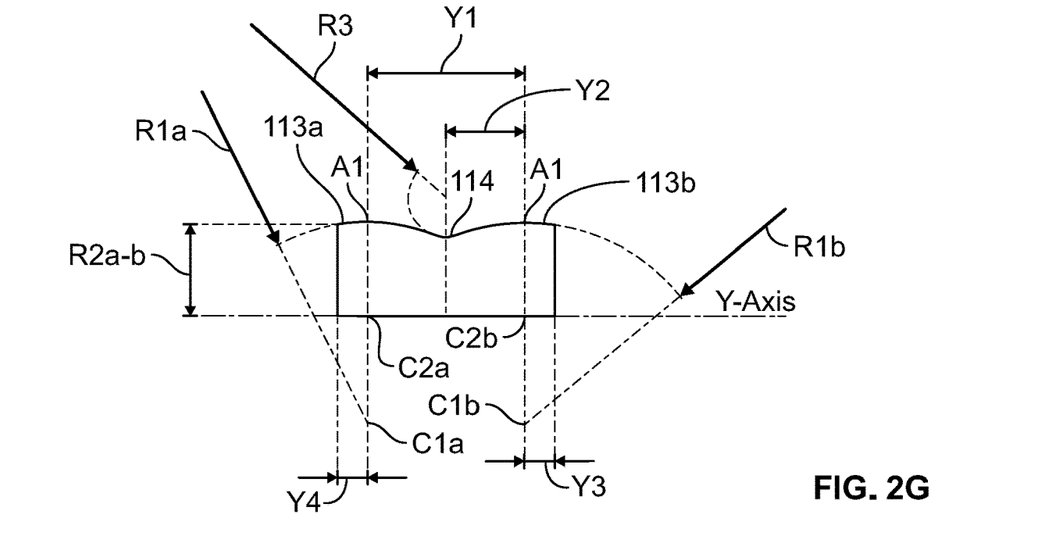
FIG. 2G is a schematic rear elevational view of the talar component of FIG. 2A.

FIG. 2G depicts the configuration of articular surfaces 113a-b based on the spheroid described above. In this regard, as previously mentioned, articular surfaces 113a-b are convex with a concave intercondylar notch 114 therebetween. Intercondylar notch 114 is concavely curved such that it has a constant radius of curvature R3 as notch 114 sweeps in the A-P direction along talar component 110.

Lateral articular surface 113a is a revolved spheroidal arc that convexly curves in the coronal plane about a first center of curvature C1a so as to define a first radius of curvature R1a and in the sagittal plane about a second center of curvature C2a so as to define a second radius of curvature R2a, where the first radius of curvature R1a is greater than the second radius of curvature R2a. Medial articular surface 132b similarly is a revolved spheroidal arc that is convexly curved in the coronal and sagittal planes about first and second centers of curvature C1b, C2b so as to define respective first and second radii of curvature R1b, R2b where the first radius of curvature R1b is greater than the second radius of R2b. Such radii of curvature R1a-b, R2a-b can be adjusted so as to be sized specifically to the particular patient or to correlate to incremental sized implants (e.g., X-small, small, large, etc.) for general populations of patients. For example, the depicted embodiment is exemplary of a talar component for a human of average size and has first centers of curvature R1a-b that are about 50 mm and second centers of curvature R2a-b that are about 23 mm. However, in other embodiments, first centers of curvature R1a-b can be 40 mm to 60 mm, and second centers of curvature R2a-b can be 10 mm to 35 mm Thus, in the embodiment depicted, lateral and medial condyles 112a-b have the same radii of curvature R1a-b, R2a-b. However, in some embodiments, the radii of curvature R1a-b, R2a-b between lateral and medial condyles 112a-b may differ. For example, where talar component 110 pivots about a medial axis normal to medial condyle 112b, as described below, lateral condyle 112a may have a larger first and/or second radius of curvature R1a, R2a than that of medial condyle 112b. In other embodiments, such as where talar component 110 pivots about a lateral axis normal to lateral condyle 112a, as also described below, medial condyle 112b may have a larger first and/or second radius of curvature R1b, R2b than lateral condyle 112a. In addition, in some embodiments the first radius of curvature R1a-b of lateral and/or medial condyle 112a-b may be equal to that of second radius of curvature R2a-b such that lateral and/or medial condyle 112a-b forms a sphere or is spherical. In other words, lateral and medial condyles 112a-b may each have the same radius of curvature in both the coronal and sagittal planes.

Also, as shown, the first centers of curvature C1a-b of lateral and medial condyles 112a-b are coaxial but offset in a superior-inferior direction. A first distance Y1 along the Y-Axis separates centers of curvature C1a-b, C2a-b of lateral and medial condyles 112a-b, and a second distance Y2 separates a centerline of talar component 110 and first centers of curvature C1a-b. A third distance Y3 separates first and second centers of curvature C1a-b, C2a-b and respective lateral and medial extents of articular surfaces 132a-b. In the embodiment depicted, Y2 is half of Y1 such that centers of curvature C1a, C2a of lateral condyle 112a are equally spaced to that of medial condyle 112b from the centerline that passes through intercondylar notch 114. Moreover, Y2 remains constant in the A-P direction such that lateral and medial condyles 112a-b are parallel. However, in some embodiments, condyles 112a-b may diverge such that Y2 remains half of Y1 but becomes larger either anteriorly or posteriorly. Also, Y3 is smaller than Y2 which, as indicated above, is smaller than Y1. Second centers of curvature C2a-b both lie on Y-Axis and are positioned between first centers of curvature C1a-b and their respective articular surfaces 113a-b. Thus, lateral and medial condyles 112a-b curve in an A-P direction about Y-Axis. In this regard, dorsal and plantar flexion, as defined by articular surfaces 113a-b, occurs about Y-Axis.

Figure 3A:
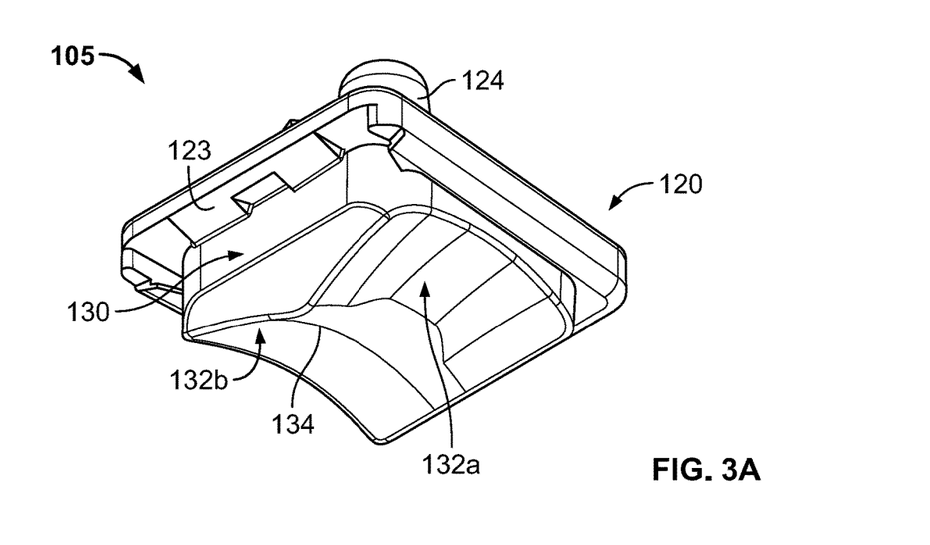
FIG. 3A is a front perspective view of the tibial component of the total ankle prosthesis of FIG. 1A.
Figure 3B:
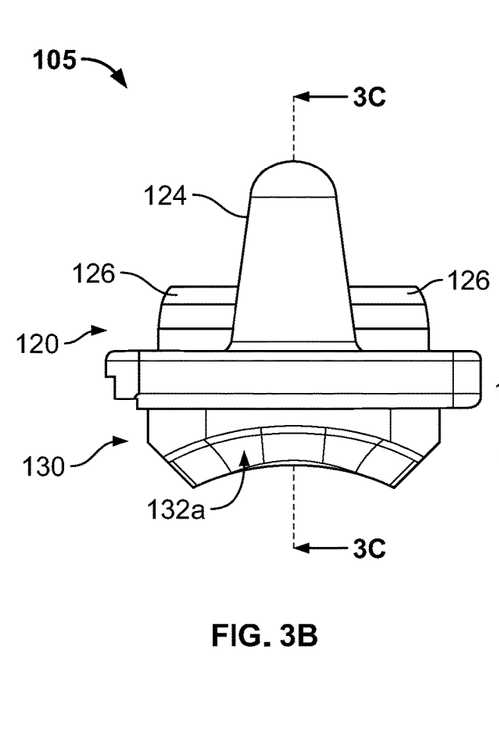
FIG. 3B is a side elevational view of the tibial component of FIG. 2A.
Figure 3C:
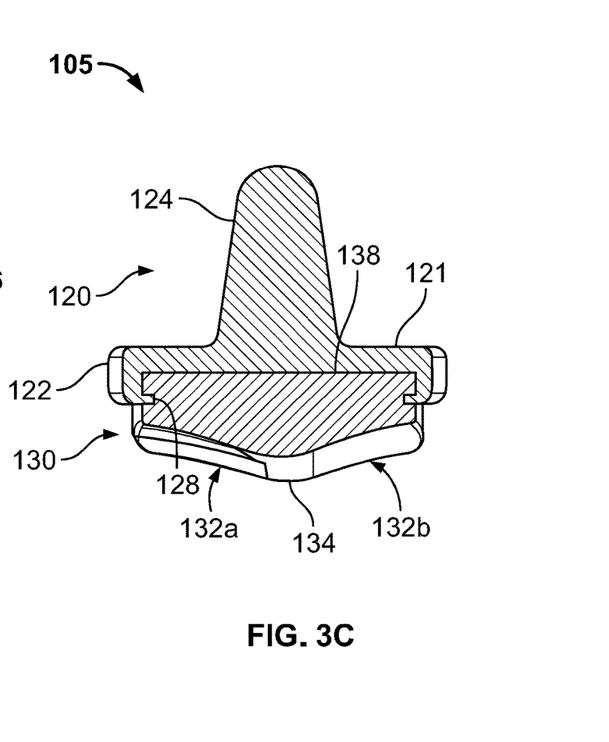
FIG. 3C is a cross-sectional view taken along line A-A of FIG. 3B.

Tibial baseplate 120 includes a plate portion 122, a stem 124, and keels 126. Plate portion 122 has a bone contacting surface 121, an insert facing surface 123, and a rim 128, as best shown in FIGS. 3A-3C. Stem 124 extends from bone contacting surface 121 and is conically tapered for a press-fit into a tibia. Keels 126 extend outwardly from stem 124 and superiorly from bone contacting surface 121. Insert facing surface 123 is substantially planar. Rim 128 is offset in an inferior direction from insert facing surface 123 and projects radially inwardly. In addition, rim 128 extends along lateral, medial, and posterior sides of plate portion 122. However, rim 128 does not extend along an anterior side of plate portion 122. Rim 128 and insert facing surface 123 define a groove for receipt of a flange 136 of tibial insert 130, as described below. The absence of rim 128 at the anterior side of plate portion 122 creates a clearance opening for tibial insert 130 to be received within the groove.

Tibial insert 130 includes a baseplate facing surface 138 (see FIG. 3C) and an articular side. Baseplate facing surface 138 is planar so as to interface with insert facing surface 123 of baseplate plate portion 122. In addition, a groove 132 extends inwardly from a sidewall surface of insert 130 and extends along posterior, lateral, and medial sides of thereof. A flange 136 is defined between groove 131 and baseplate facing surface 138. Such flange 136 is received within the groove of baseplate 120 while rim 128 is received in groove 131 of insert 130, as best shown in FIG. 3C.

The articular side of tibial insert 130 includes a first condyle or lateral condyle 132a and a second condyle or medial condyle 132b. Lateral and medial condyles 132a-b are separated by an intercondylar spine 134 that projects inferiorly away from baseplate facing surface 138 and defines a location of maximum thickness of insert 130.

Medial condyle 132b is a concave surface that is bounded by a condylar edge 154. Such condylar edge 154 defines a perimeter of medial condyle 132b and is comprised of an anterior edge 154a, posterior edge 154p, medial edge 154m, and lateral edge 154l. Medial edge 154m in this embodiment refers to the interface between spine 134 and medial condyle 132b. Stated another way, in the particular embodiment depicted, spine 134 ends where medial condyle 132b begins. The A-P interface between intercondylar spine 134 and medial condyle 132b is medial edge 154m of medial condyle 132b. However, in some other embodiments, a flat surface may extend between spine 134 and condylar edge 154m such that spine 134 and condylar edge 154m of medial condyle 132b do not interface. Also, in the embodiment depicted, medial condyle 132b includes a single articular portion 150 that is a spheroidal surface defined by the prolate spheroid of FIGS. 2D-2F. In this regard, spheroidal articular portion 150 extends between and intersects anterior and posterior edges 154a, 154p and also lateral and medial edges 154l, 154m and has a second curvature with a second radius of curvature R2b between anterior and posterior edges 154a, 154p and a first curvature with a first radius of curvature R1b between lateral and medial edges 154l, 154m, as best shown in FIG. 4E. R1b is larger than R2b, but may be equal in some embodiments. In other words, medial condyle 132b is concavely curved in both a sagittal and coronal plane and the radii of curvature differ in both planes. However, similar to that of talar condyles 112a-b, medial condyle 132b is in the form of an elongate, revolved spheroidal arc such that the arc length of spheroidal surface 150 in the A-P direction is longer than in a lateral-medial direction. The radii of curvature R1b, R2b of medial condyle 132b is effectively equal to that of medial condyle 112b of talar component 110 such that when medial condyles 112b and 132b articulate and are in direct contact with each other, the spheroidal convex and concave surfaces 113b, 150 of such condyles 112b, 132b are congruent in both sagittal and coronal planes so as to form area-contact. This is illustrated in the cross-sections of FIGS. 5D-5F, which are described further below.

Lateral condyle 132a is a concave surface that is bounded by a condylar edge 144. Such condylar edge 144 defines a perimeter of lateral condyle 132a and is comprised of an anterior edge 144a, posterior edge 144p, medial edge 144m, and lateral edge 144l. Medial edge 144m in this embodiment refers to the interface between spine 134 and lateral condyle 132a. Stated another way, in the particular embodiment depicted, spine 134 ends where lateral condyle 132a begins. The A-P interface between intercondylar spine 134 and lateral condyle 132a is the medial edge 144m of lateral condyle 132a. However, in some other embodiments, a flat surface may extend between spine 134 and condylar edge 144m such that spine 134 and condylar edge 144m of lateral condyle do not interface.

Figures 4A, 4B, 4C:
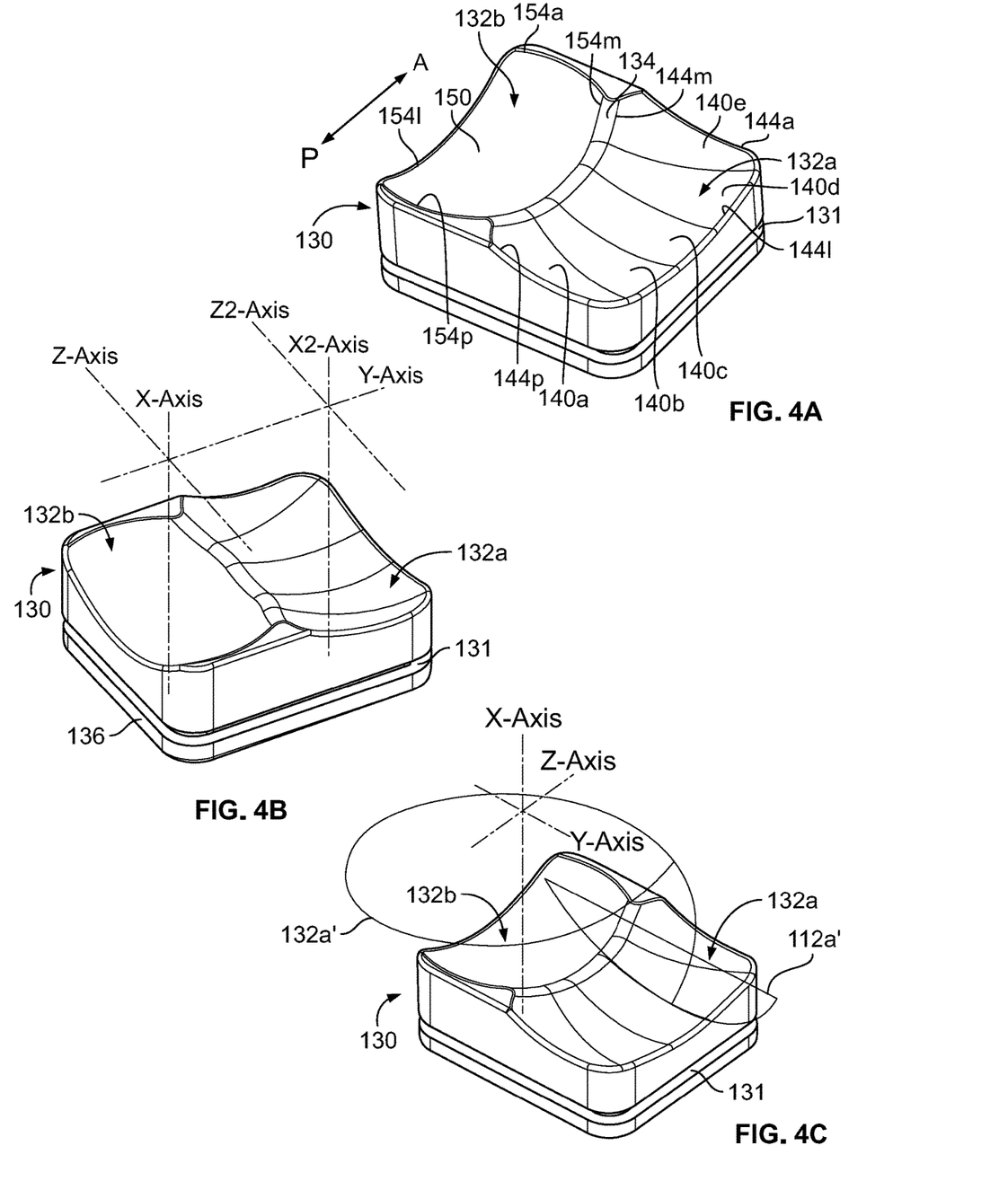
FIGS. 4A-4C are bottom perspective views of a tibial insert of the tibial component of FIG. 2A.
Figure 4D:
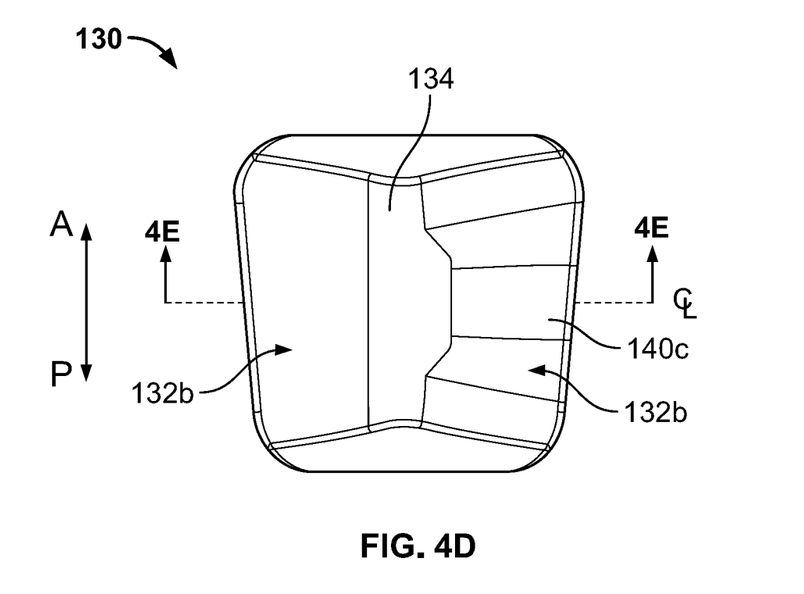
FIG. 4D is a bottom view of the tibial insert of FIGS. 4A-4C.
Figure 4E:
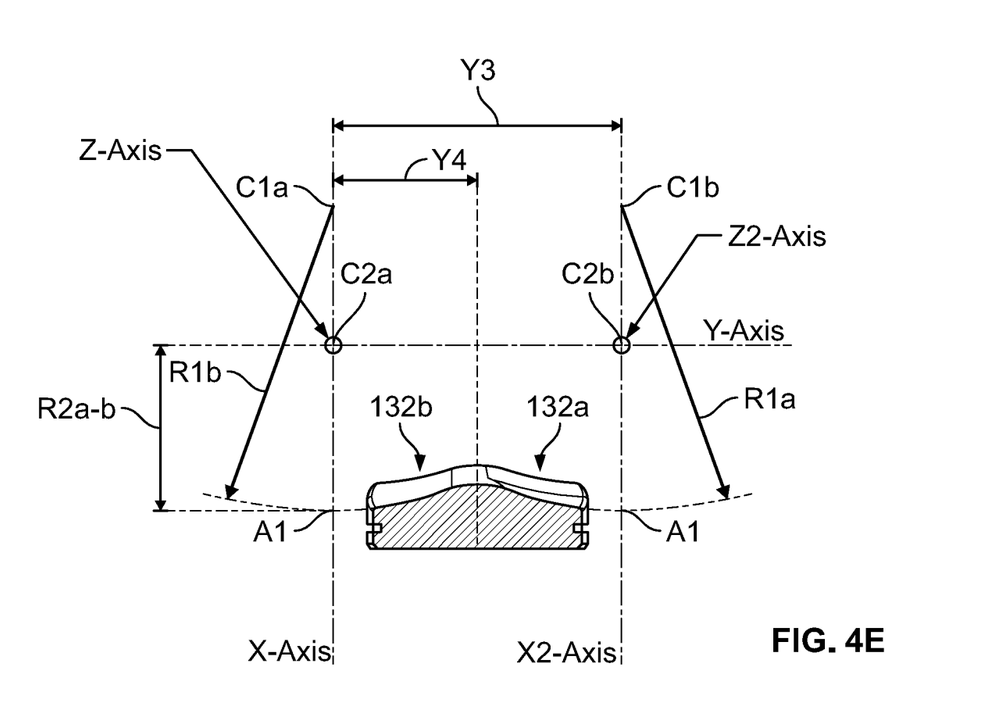
FIG. 4E is a cross-sectional view taken along the center line E-E of FIG. 4D.

As shown, lateral condyle 132a includes a plurality of articular portions 140 positioned within the boundary of condylar edge 144, as best shown in FIG. 4A. In particular, lateral condyle 132a includes first, second, third, fourth, and fifth articular portions 140a-e. Such portions are configured to provide a particular articulation profile with lateral condyle 112a of talar component 110. For example, in the embodiment depicted, first, third, and fifth articular portions 140a, 140c, 140e are spheroidal surfaces. In addition, second and fourth articular portions 140b, 140d are cylindrical surfaces defined by a cylindrical helix 132a'. Since first, third, and fifth articular portions 140a, 140c, 140e are spheroidal surfaces, such surfaces are each concavely curved in coronal and sagittal planes. More specifically articular portions 140a, 140c, and 140e are defined by the same prolate spheroid shown in FIGS. 2D-2F that defines lateral condyle 112a of talar component 110 such that the radii of curvature in the sagittal and coronal planes differ so that a first radius of curvature R1a is larger than a second radius of curvature R2a, as best shown in FIGS. 4D and 4E. Thus, in the embodiment depicted, spherical articular portions 140a, 140c, 140e have the same radii of curvature. Furthermore, the radii of curvature R1a, R2a of spheroidal articular portions 140a, 140c, and 140e are congruent to that of spheroidal surface 113a of lateral condyle 112a of talar component 110. Thus, the radii of curvature R1a, R2a of each of spheroidal articular portions 140a, 140c, 140e of tibial insert 130 are respectively equal to the first and second radii of curvature R1a, R2a of lateral condyle 112a of talar component 110, although the corresponding radii of curvature R1a, R2a of lateral condyle 112a of talar component 110 might be slightly smaller than that of each of the spheroidal articular portions 140a, 140c, 140e to account for manufacturing tolerances. Thus, when lateral condyle 112a of talar component 110 articulates or is in direct contact with any of spheroidal articular portions 140a, 140c, 140e, area-contact is formed such that loads are distributed over the spheroidal areas provided by lateral condyles 112a and 132a. However, first and fifth articular portions 140a and 140e may have different radii of curvature than third articular portion 140c provided that the radii of curvature of third articular portion 140c is congruent with that of lateral condyle 112a of talar component.

As mentioned above, cylindrical articular portions 140b, 140d are defined by a cylindrical helix 132a'. Such cylindrical helix 132a', as illustrated in FIG. 4C, extends about an "X-Axis" that is normal to medial condyle 132b. Such X-Axis is located at a geometric center of medial condyle 132b, as best shown in FIG. 4E. Thus, second and fourth articular portions 140b, 140d have a curvature that bends about X-Axis. Such curvature forms an arcuate path for lateral condyle 112a of talar component 110 when articulating with lateral condyle 132a of tibial insert 130. Due to the helix 132a' extending about X-Axis, a constant distance between lateral and medial condyles 132a-b is maintained. Such distance is illustrated in FIG. 4E between the X-Axis of medial condyle 132b and "X2-Axis" normal to or coincident with lateral condyle 132a. In other words, X2-Axis is intersects the geometric centers C1a and C2a of lateral condyle 132a. The geometric centers C1a, C2a of lateral condyle 132a lie in a plane that cuts through the center of third articular portion 140c. It should be noted that the geometric centers C1a-b, C2a-b of lateral and medial condyles 132a-b of tibial insert 130 are laterally and medially offset from the physical structure of tibial insert 130, as shown in FIG. 4E, while the correspondent geometric centers C1a-b, C2a-b of lateral and medial condyles 112a-b of talar component 110 are intersected by an axis that intersects the physical structure of talar component 110, as best shown in FIG. 2G. In other words, condyles 132a-b of tibial component are defined by a different section of the prolate spheroid than condyles 112a-b such that the coronal and sagittal plane apices (A1, A2) of the prolate spheroid are included in the structure of talar component 110 while being offset from the structure of the tibial component. However, in some embodiments, centers C1a-b, C2a-b may be centered directly over their respective tibial condyles 132a-b. Moreover, the distance Y3 between the centers C1a-b, C2a-b of tibial insert 130 is greater than such correspondent distance Y1 of talar component 110. However, the distance Y4 between a center line of insert 130 and centers C1a-b, C2a-b is half of Y3 just as Y2 is half of Y1.

Cylindrical helix 132a' also has a cylindrical radius of curvature that defines the convex curvature of cylindrical articular portions 140b, 140d between medial and lateral condylar edges 144m, 144l, which is illustrated by the semi-circular overlay 112a' in FIG. 4C representing the cylindrical curvature of condyle 132a in a coronal plane. Thus, second and fourth articular portions 140b, 140d have a radius of curvature in a coronal plane and no radius of curvature in a sagittal plane. The radius of curvature of second articular portion 140b is preferably equal to that of fourth articular portion 140d. In addition, the radii of curvature of cylindrical articular portions 140b, 140d are preferably equal to first radius of curvature R1a of spheroidal articular portions 140a, 140c, and 140e. Thus, when lateral condyle 112a of talar component 110 articulates with or is in direct contact with any of cylindrical articular portions 140b, 140d, line-contact is formed. Such line-contact extends between medial and lateral edges 144m and 144l of lateral condyle 132a. Also, cylindrical helix 132a' may have a shallow or steep slope such that the elevational difference between second and fourth articular portions 140b, 140d is either de-minimis or significant to affect articulation. In this regard, as described below, when the slope of helix 132a' is significant, the elevational difference between second and fourth articular portions 140b, 140d induces eversion and inversion of a foot.

Articular portions 140a-e are arranged such that third articular portion 140c is positioned between second and fourth articular portions 140b, 140d while first and fifth articular portions 140a, 140e respectively intersect posterior and anterior condylar edges 144p, 144a. Thus, cylindrical articular portions 140b, 140d are bounded at both of their A-P ends by spheroidal articular portions 140a, 140c, and 140e. However, second and fourth articular portions 140b, 140d are tangent to third articular portion 140c and respectively to first and fifth articular portions 140a, 140e so as to create a smooth transition between each articular portion. It should be noted that FIGS. 4A-4B depict tibial insert 130 flipped upside down relative to its implanted position in which the articular side thereof would face inferiorly.

Figure 5A:
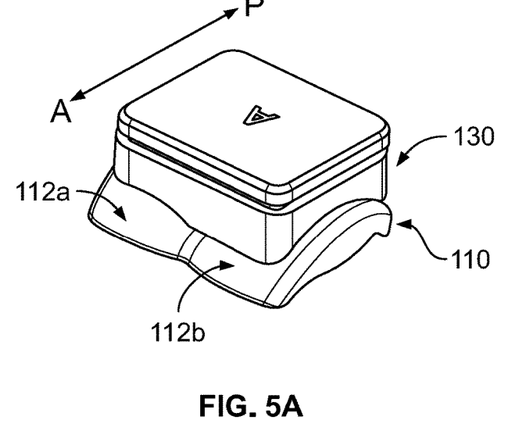
FIG. 5A is a front perspective view of an assembly of the talar component of FIG. 2A and the tibial insert of FIGS. 4A-4E.
Figure 5B:
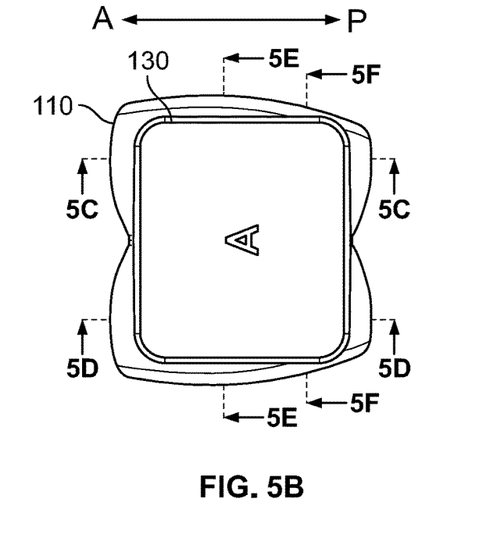
FIG. 5B is a top view of the assembly of FIG. 5A.
Figure 5C:
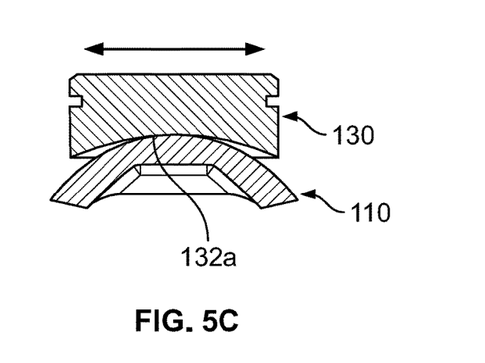
FIG. 5C is a cross-sectional view taken along the line C-C of FIG. 5B.
Figure 5D:
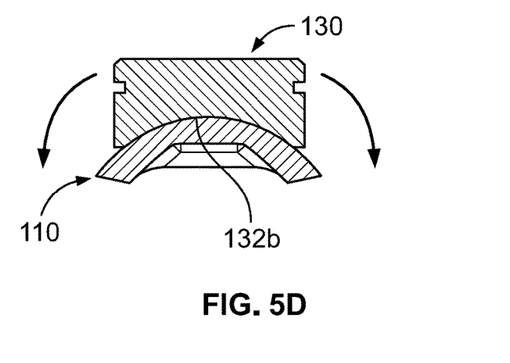
FIG. 5D is a cross-sectional view taken along the line D-D of FIG. 5B.
Figure 5E:
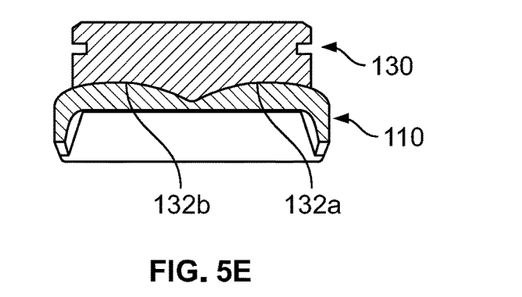
FIG. 5E is a cross-sectional view taken along the line E-E of FIG. 5B.
Figure 5F:
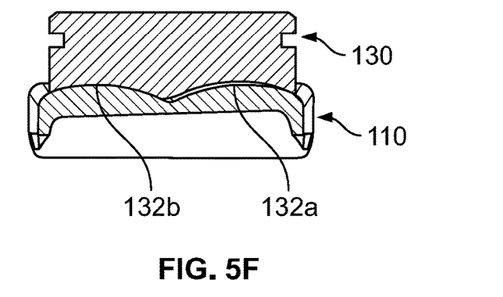
FIG. 5F is a cross-sectional view taken along the line F-F of FIG. 5B.

FIGS. 5A-5F depict tibial insert 130 and talar component 110 interfacing in a neutral position. In the neutral position, medial condyles 112b, 132b are congruent in both sagittal and coronal planes, as shown in FIGS. 5D-5F. This congruity is due to the medial condyles 112b, 132b having the same or approximately the same radii of curvature and constrains medial condyles 112b, 132b from relative translational movement and also distributes loads along the spheroidal surfaces 113b, 150 of the condyles 112b and 132b creating an area-contact in both the sagittal and coronal planes. Thus, as illustrated by the arrows in FIG. 5D, in plantarflexion or dorsiflexion, tibial insert 130 slides along spheroidal surface 113b in an arc in the A-P direction about the center of curvature of medial condyle 113b of talar component 110. However, through this range of motion, contact between medial condyles 112b and 132b remains area-contact.

When lateral condyle 112a of the talar component 110 is in the neutral position, the sphericity of lateral talar condyle 112a as well as the sphericity of the corresponding third articular portion 140c of tibial condyle 132a creates a congruity in which the curvatures of condyles 112a and 132a conform in both the coronal and sagittal planes to form area-contact in both the sagittal and coronal planes, as best shown in FIG. 5C. However, in plantarflexion or dorsiflexion, cylindrical articular portions 140b and 140d provide an incongruity in the sagittal plane as also shown in FIGS. 5C and 5F that un-constrains lateral condyles 112a and 132a so that A-P translation and internal-external rotation is permitted, as illustrated by the arrows in FIG. 5C. Thus, in dorsiflexion or plantarflexion, tibial insert 130 slides over lateral talar condyle 112a. When lateral talar condyle 112a comes in contact with either second or fourth articular portion 140b, 140d, spheroidal surface 113a of the talar component is congruent with cylindrical articular portion 140b or 140d in a coronal plane so as to form line-contact, but is incongruent in a sagittal plane thus allowing for A-P translation and internal-external rotation. In the particular embodiment depicted, tibial insert 130 provides for area contact between lateral condyles 112a and third articular portion 140c from the neutral position to about ±7.5 degrees of dorsal/planter flexion. Beyond this angle of flexion, lateral condyle 112a contacts second or fourth articular portions 140b, 140d to allow for the A-P translation and internal-external rotation mentioned above. Second and fourth articular portions 140b and 140d may provide −2 degrees of internal rotation to 3 degrees of external rotation to account for weight bearing conditions. However, such articular portions 140b and 140d may be configured to provide −2 degrees of internal rotation to 8 degrees of external rotation to mimic a natural gait cycle. In instances where flexion is so deep that lateral condyle 112a articulates beyond second and fourth articular portions 140b, 140d, lateral condyle 112a will contact first or fifth articular portions 140a, 140e which act as back-stops to prevent lateral condyle from translating/rotating off of talar component 110.

Figure 6A:
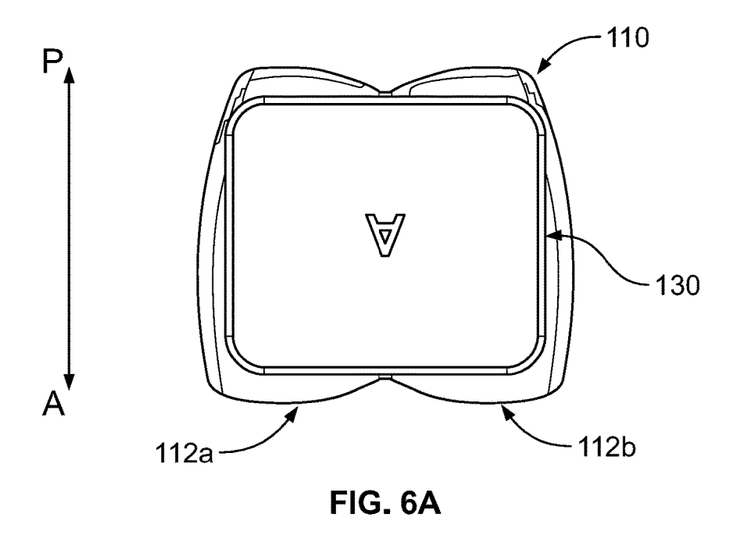
FIGS. 6A-6C is a top view of the assembly of FIG. 5A in various stages of relative movement.
Figure 6B:
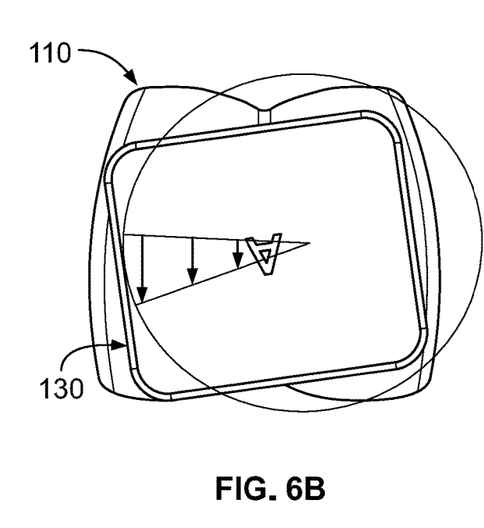
Figure 6C:
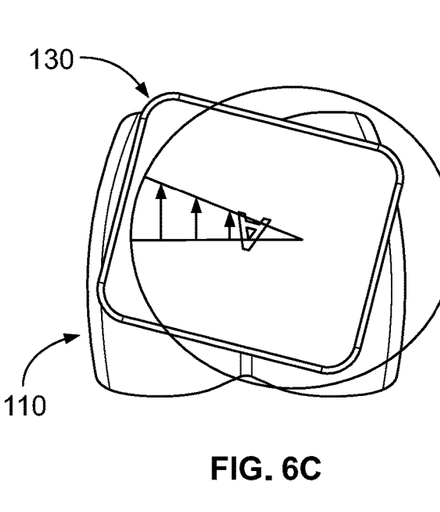

Moreover, the helical curvature of lateral condyle 132a by virtue of cylindrical articular portions 140b and 140d in conjunction with the constraint of medial condyles 112b and 132b allows lateral condyle 132a to rotate/pivot about the X-Axis. This internal-external rotation is depicted in FIGS. 6B and 6C from the neutral position which is shown in FIG. 6A. In addition, depending on the slope of cylindrical helix 132a' that defines cylindrical articular portions 140b and 140d, fourth articular portion 140d may be more inferior than second articular portion 140b. In this regard, as lateral talar condyle 112a glides into contact with fourth articular portion 140d, it may be forced inferiorly to provide for inversion of the foot. Conversely, as lateral talar condyle glides 112a into contact with second articular portion 140b, lateral condyle 132a is moved superiorly to provide for eversion of the foot.

Thus, total ankle prosthesis 100 provides three degrees of freedom: internal/external rotation about a pivot axis normal to medial condyle 132b, A-P translation of lateral condyles 112a and 132b, and dorsiflexion/plantarflexion. Additionally, and optionally, prosthesis 100 may provide for inversion and eversion. Such degrees of freedom mimic those of the natural tibiotalar joint while spreading received loads over the articular surfaces of total ankle prosthesis 100 to minimize wear. Also, while tibial insert 130 is described as being configured to allow for pivoting about X-Axis, it should be understood that tibial insert 130 could be oppositely configured such that the features of lateral and medial condyles 132a-b are swapped in order to provide for pivoting about X2-Axis.

Figure 7:
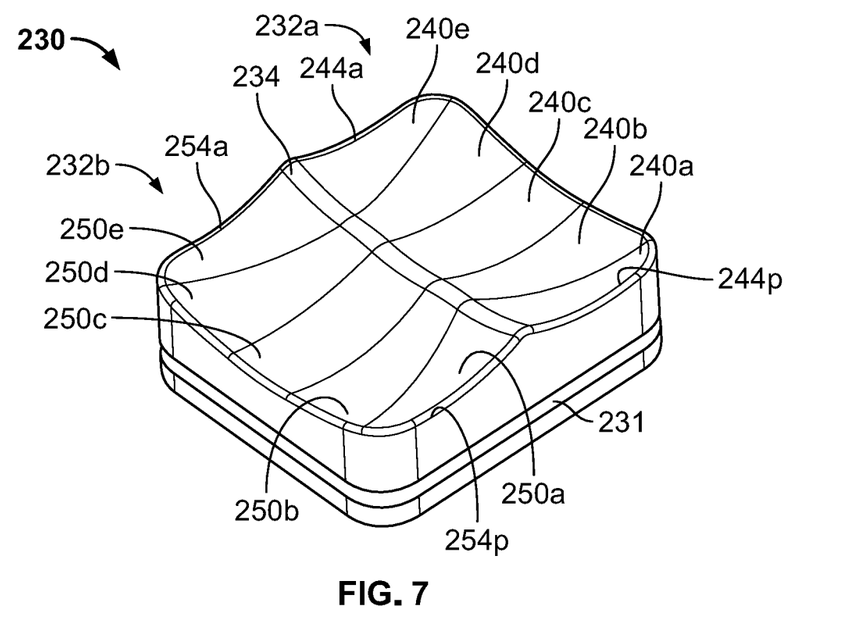
FIG. 7 is a bottom perspective view of a tibial insert according to another embodiment of the present disclosure.

FIG. 7 depicts a tibial insert 230 according to another embodiment of the present disclosure. For ease of review, like elements are accorded like reference numerals to that of tibial insert 130, but within the 200-series of numbers. For instance, tibial insert 230 includes an articular side that has lateral and medial condyles 232a-b separated by an intercondylar spine 234. Lateral and medial condyles 132a-b are concave surfaces each bounded by a condylar edge 244, 254. Moreover, lateral condyle 232a is the same as that of insert 130 in that it includes a plurality of articular portions 240-ae which comprise spheroidal articular portions 240a, 240c, 240d and helical cylindrical portions 240b, 240d. However, medial condyle 231b, instead of being comprised of a single spheroidal articular portion, is the mirror image of lateral condyle 232a in terms of the inclusion of spheroidal and cylindrical articular portions 250a-e and their arrangement. This configuration, allows both medial and lateral condyles 232a-b of tibial insert 230 and talar component 110 to experience area and line contact. In addition, medial and lateral talar condyles 112a-b can translate in an A-P direction while medial talar condyle 112b can rotate internally/externally about an X2-Axis, such as the one shown in FIG. 4B, and lateral talar condyle 112a can rotate internally/externally about an X-Axis, such as the one shown in FIG. 4B, that is normal to medial condyle 232b.

Figure 8:
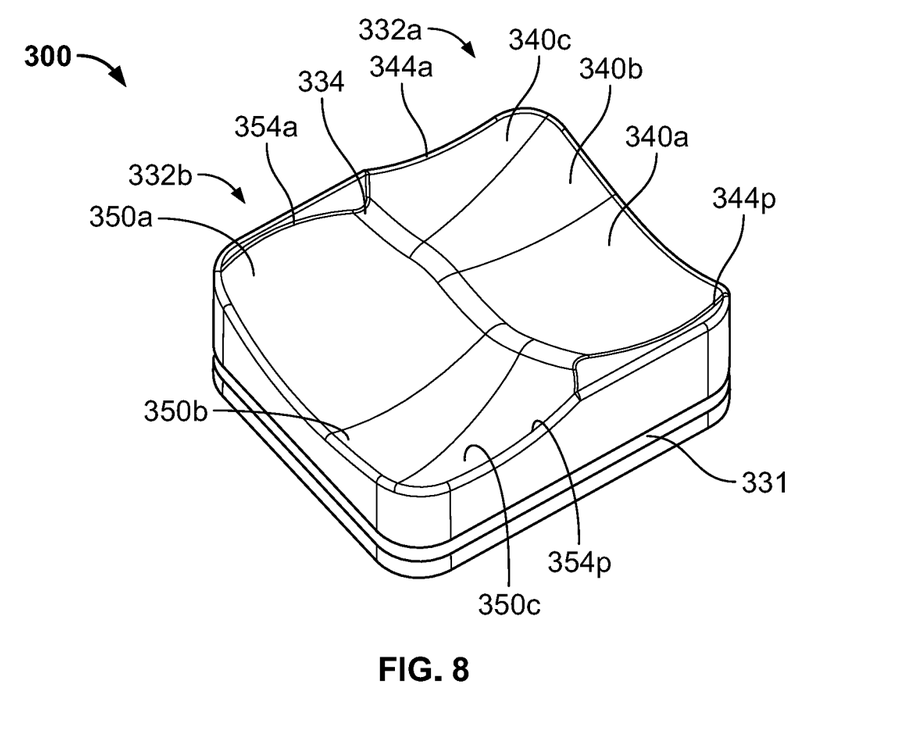
FIG. 8 is a bottom perspective view of a tibial insert according to a further embodiment of the present disclosure

FIG. 8 depicts a tibial insert 330 according to another embodiment of the present disclosure. For ease of review, like elements are accorded like reference numerals to that of tibial insert 130, but within the 300-series of numbers. For instance, tibial insert 330 includes an articular side that has lateral and medial condyles 332a-b separated by an intercondylar spine 334. Lateral and medial condyles 332a-b are concave surfaces each bounded by a condylar edge 340, 350. However, unlike insert 130, both lateral and medial condyles 332a-b only include first, second, and third articular portions 340a-c, 350a-c. In addition, articular portions 350a-c of medial condyle 332a are oppositely arranged relative to that of lateral condyle 340a-c. In this regard, first and third articular portions 340a, 340c of lateral condyle 332a respectively intersect posterior and anterior condylar edges 344p, 344a, while first and third articular portions 350a, 350c of medial condyle 332b respectively intersect anterior and posterior condylar edges 354a, 354p. Moreover, first articular portions 340a and 350a extend over half of the A-P length of medial and lateral condyles 332a-b. First and third articular portions 340a, 340c, 350a, 350c of both lateral and medial condyles 332a-b are spheroidal, and second articular portions 340b, 350b of lateral and medial condyles 332a-b are each defined by a cylindrical helix. The radii of curvature of such articular portions 340a-c, 350a-c are consistent with the description above relative to insert 130 such that the radii of curvature of articular portions 340a-c and 350a-c are congruent with that of talar component 110.

Figure 9:
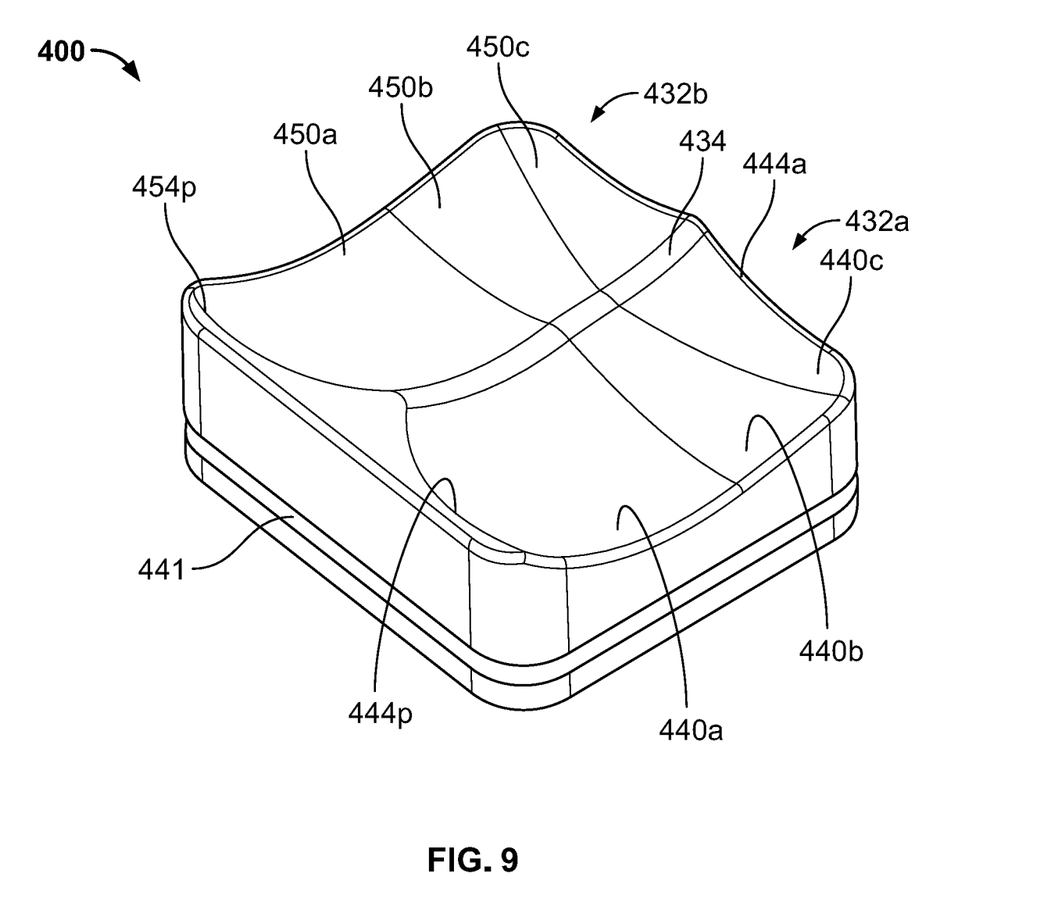
FIG. 9 is a bottom perspective view of a tibial insert according to an even further embodiment of the present disclosure

FIG. 9 depicts a tibial insert 430 according to another embodiment of the present disclosure. For ease of review, like elements are accorded like reference numerals to that of tibial insert 130, but within the 400-series of numbers. Insert 430 is similar to insert 330 with the only difference being that the medial condyle 432b is a mirror image of the lateral condyle 432a such that first, second, and third articular portions 450a-b of medial condyle 432b are similarly arranged to that of lateral condyle 432a. In this regard, first articular portions 440a and 450a, which are spheroidal, intersect posterior edges 444P and 454P, respectively, while third articular portions 440c and 450c, which are also spheroidal, intersect anterior edges 444a and 454a, respectively. Moreover, first articular portions 440a and 450a extend over half of the A-P length of medial and lateral condyles 432a-b.

While the foregoing describes several embodiments of a total ankle prosthesis, it should be understood that the described characteristics of such embodiments can be applied to other prostheses, such as those for knees, fingers, and elbows, with modifications made thereto to account for size differences and other features of the particular joint. For example, a total knee prosthesis may have a femoral component having lateral and medial condyles with spheroidal surfaces similar to that of talar component 110, but having larger radii of curvatures than described herein. In addition, such knee prosthesis may have a tibial component with a tibial baseplate and a polymer tibial insert, as is commonly understood in the art. Moreover, the tibial insert may have lateral and medial condyles configured similarly to that of the foregoing embodiments for articulation with the femoral component. In this regard, the lateral and/or medial condyles of the tibial insert may have spheroidal and cylindrical helical portions arranged as described herein so that an internal/external rotational pivot axis is normal to the opposing condylar surface.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A total ankle prosthesis comprising:
   a talar component having a bone contacting side for contacting a talus and an articular side opposite the bone contacting side, the articular side having first and second condyles separated by an intercondylar notch, the first condyle defining a spheroidal convex surface;
   a tibial component having a bone contacting side for contacting a tibia and an articular side, the articular side having first and second condyles separated by an intercondylar spine, the first condyle of the tibial component defining a concave surface, the concave surface having a condylar edge defining a perimeter thereof and a plurality of articular portions positioned between anterior and posterior extents of the condylar edge, a first articular portion of the articular portions being spheroidal and a second articular portion being defined by a cylindrical helix.

2. The total ankle prosthesis of claim 1, wherein the tibial component includes a tibial baseplate and a tibial insert connectable to the tibial baseplate, the tibial baseplate including the bone contacting side of the tibial component and the tibial insert including the articular side of the tibial component.

3. The total ankle prosthesis of claim 1, wherein the first condyle of the tibial component is a medial condyle.

4. The total ankle prosthesis of claim 1, wherein first condyle of the tibial component is a lateral condyle.

5. The total ankle prosthesis of claim 1, wherein the concave surface of the first condyle has a third articular portion defined by the cylindrical helix that defines the second articular portion, the first articular portion being positioned between the second and third articular portions.

6. The total ankle prosthesis of claim 5, wherein the concave surface has fourth and fifth articular portions each being spheroidal, the fourth and fifth articular portions being positioned so that they respectively intersect the anterior and posterior extents of the condylar edge.

7. The total ankle prosthesis of claim 6, wherein the second condyle of the tibial component is arranged identically to that of the first condyle.

8. The total ankle prosthesis of claim 5, wherein the first, second, and third articular portions each have a curvature that extends between lateral and medial extents of the condylar edge of the first condyle, the curvatures of the first, second, and third articular portions each defining a radius of curvature, the radii of curvatures of the first, second, and third articular portions being equal.

9. The total ankle prosthesis of claim 5, wherein the second and third articular portions slope downwardly in a posterior to anterior direction such that, when the tibial component is implanted, the second articular portion is positioned more inferiorly than the third articular portion.

10. The total ankle prosthesis of claim 1, wherein the curvature of the convex surface of the first condyle of the talar component is such that, when the first condyle of the talar component articulates with the first condyle of the tibial component, a first interface between the first condyle of the talar component and the first articular portion forms area contact, and a second interface between the first condyle of the talar component and the second articular portion forms line contact that extends between lateral and medial extents of the condylar edge.

11. The total ankle prosthesis of claim 1, wherein the second condyle of the talar component defines a spheroidal convex surface, and the second condyle of the tibial component defines a concave surface that has a condylar edge defining a perimeter thereof and a first articular portion.

12. The total ankle prosthesis of claim 11, wherein the first articular portion of the second condyle is spheroidal and has a curvature that extends from an anterior extent to a posterior extent of the condylar edge of the second condyle.

13. The total ankle prosthesis of claim 11, wherein the concave surface of the second condyle of the tibial component includes a second articular portion, the first articular portion of the second condyle of the tibial component being spheroidal and the second articular portion of the second condyle of the tibial component being defined by a cylindrical helix.

14. The total ankle prosthesis of claim 11, wherein the spheroidal convex surface of each of the first and second condyles of the talar component has an arc length in an anteroposterior direction longer than an arc length in a lateral-medial direction.

15. A total ankle prosthesis comprising:
a talar component having a bone contacting side for contacting a talus and an articular side opposite the bone contacting side, the articular side having lateral and medial condyles separated by an intercondylar notch, the lateral condyle defining a spheroidal convex surface;
a tibial component having a bone contacting side for contacting a tibia and an articular side, the articular side having lateral and medial condyles separated by an intercondylar spine, the lateral condyle of the tibial component defining a concave surface having a condylar edge defining a perimeter thereof and a plurality of articular portions positioned between anterior and posterior extents of the condylar edge, a first articular portion of the articular portions being spheroidal such that it has a radius of curvature in both a coronal and sagittal plane, and a second articular portion of the articular portions being cylindrical such that it has a radius of curvature in a coronal plane but not in a sagittal plane.

16. The total ankle prosthesis of claim 15, wherein the radii of curvatures of the first and second articular portions in the coronal plane are equal.

17. The total ankle prosthesis of claim 16, wherein the spheroidal convex surface of the lateral condyle of the talar component is congruent with the first articular portion.

18. The total ankle prosthesis of claim 15, wherein the medial condyle of the talar component defines a spheroidal convex surface, and the medial condyle of the tibial component defines a concave surface having a condylar edge defining a perimeter thereof and a spheroidal articulation portion that extends between anterior and posterior extents of the condylar edge of the medial condyle, the spheroidal convex surface of the medial condyle being congruent with the spheroidal articulation portion.

\* \* \* \* \*